United States Patent
Lane

(10) Patent No.: US 7,335,214 B2
(45) Date of Patent: Feb. 26, 2008

(54) EXTERNAL VENOUS VALVE STENTS FOR THE CORRECTION OF INCOMPETENT VENOUS VALVES

(76) Inventor: Rodney James Lane, 141 Edinburgh Road, Castlecrag, New South Wales 2068 (AU)

( * ) Notice: Subject to any disclaimer, the term of this patent is extended or adjusted under 35 U.S.C. 154(b) by 98 days.

(21) Appl. No.: 10/472,460

(22) PCT Filed: Mar. 21, 2002

(86) PCT No.: PCT/AU02/00361

§ 371 (c)(1),
(2), (4) Date: Feb. 13, 2004

(87) PCT Pub. No.: WO02/076305

PCT Pub. Date: Oct. 3, 2002

(65) Prior Publication Data

US 2004/0133267 A1    Jul. 8, 2004

(30) Foreign Application Priority Data

Mar. 23, 2001 (AU) ..................... PR3892

(51) Int. Cl.
*A61B 17/08* (2006.01)
(52) U.S. Cl. .............. 606/151; 606/157; 606/158
(58) Field of Classification Search ................ 606/139, 606/140, 151, 157, 158
See application file for complete search history.

(56) References Cited

U.S. PATENT DOCUMENTS

| | | | |
|---|---|---|---|
| 2,756,753 A | * | 7/1956 | Means ........................ 128/885 |
| 3,435,823 A | * | 4/1969 | Edwards ..................... 606/153 |
| 4,904,254 A | * | 2/1990 | Lane .......................... 623/1.24 |
| 5,147,389 A | * | 9/1992 | Lane .......................... 623/1.24 |

(Continued)

FOREIGN PATENT DOCUMENTS

WO    WO 88/00454    1/1988

(Continued)

OTHER PUBLICATIONS

Schanzer, Harry M.D., et al. "A Rational Approach to Surgery of the Chronic Venous Stasis Syndrome," *Annals of Surgery*, vol. 195, No. 1, pp. 25-29 (Jan. 1982).

(Continued)

*Primary Examiner*—Michael J. Hayes
*Assistant Examiner*—Michael G. Mendoza
(74) *Attorney, Agent, or Firm*—Victor N. King; Speckman Law Group PLLC

(57) ABSTRACT

Improvements to external stents to render incompetent venous valves competent are disclosed. The device is an inelastic bio-compatible cuff (1) that encircles the venous valve cusps (15) decreasing the internal diameter of the vein wall (11) to allow apposition of the cusps (15) and create competence. The device may be calibrated to known diameters to create competence for different phenotypes. The different diameters are indicated by holes (2, 3, 4) in the body (1). The buckle attachment (6) allows the body of the device to become conical or inverted to become pyramidal as appropriate. The wide buckle (5) allows the device to become elliptical at smaller diameters. The angle of the notches (10) in the device is approximately 15°, which allows better overriding at the sapheno-femoral junction resulting in better competence of the valve.

20 Claims, 2 Drawing Sheets

U.S. PATENT DOCUMENTS

| | | | |
|---|---|---|---|
| 5,211,649 A | * | 5/1993 | Kohler et al. ............... 606/139 |
| 5,417,698 A | * | 5/1995 | Green et al. ................ 606/139 |
| 5,824,061 A | * | 10/1998 | Quijano et al. ............ 623/1.13 |

FOREIGN PATENT DOCUMENTS

| | | |
|---|---|---|
| WO | WO 88/06021 | 8/1988 |
| WO | WO 97/40755 | 11/1997 |

OTHER PUBLICATIONS

Hallberg, Dag "A Method for Repairing Incompetent Valves in Deep Veins," *Acta Shirurgica Scandinavica*, vol. 138, pp. 143-145 (1972).

Ferris, Eugene B., M.D. et al. "Femoral Vein Reconstruction in the Management of Chronic Venous Insufficiency," *Archives of Surgery*, vol. 117, No. 12, pp. 1571-1579 (Dec. 1982).

Raju, Seshadri M.D. "Venous Insufficiency of the Lower Limb and Stasis Ulceration," *Annals of Surgery*, vol. 197, No. 6, pp. 688-697 (Jun. 1983).

Blaisdell, William F., et al. "Revascularization of Severely Ischemic Extremities with an Arteriovenous Fistula," *American Journal of Surgery*, vol. 112, pp. 166-174 (1966).

* cited by examiner

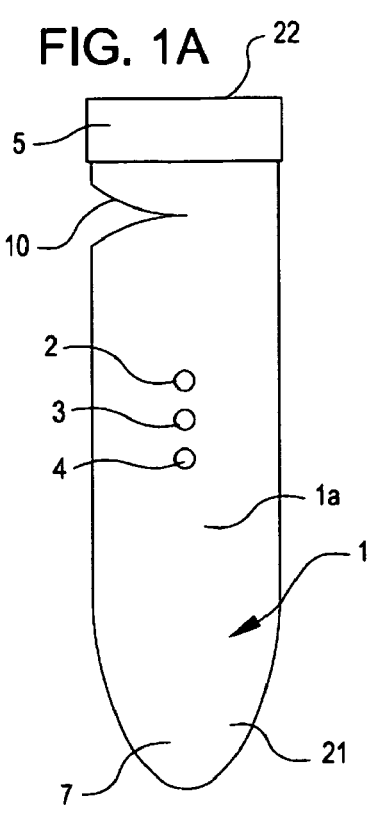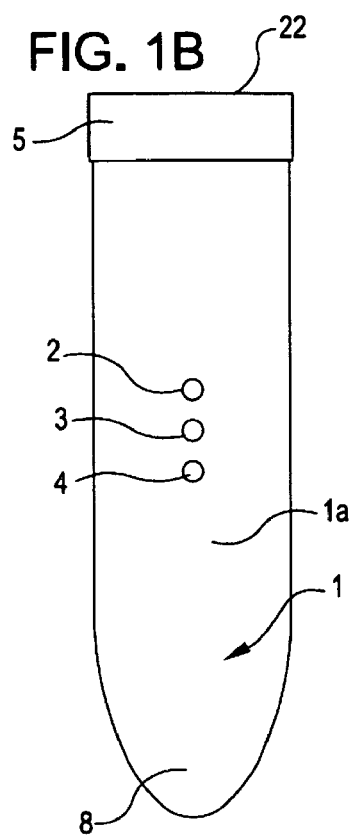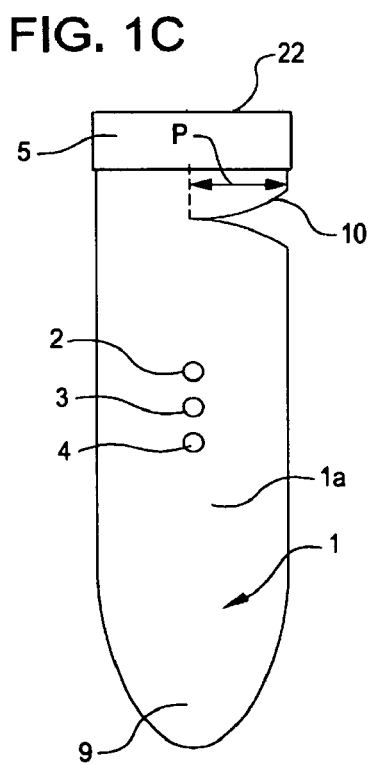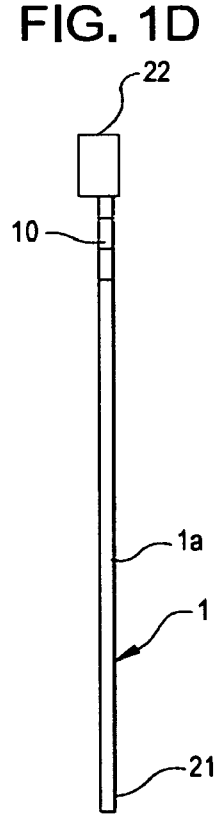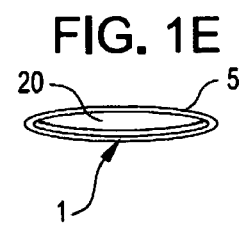

EXTERNAL VENOUS VALVE STENTS FOR THE CORRECTION OF INCOMPETENT VENOUS VALVES

FIELD OF INVENTION

This invention relates to the correction of incompetent venous valves.

BACKGROUND OF THE INVENTION

Venous valves in mammals are usually bicuspid valves, with each cusp forming a sack or reservoir for blood which, under pressure, forces the free edges of the cusps together to prevent retrograde flow of the blood and allow only antegrade flow to the heart. When an incompetent valve attempts to close in response to a pressure gradient across the valve, the cusps do not seal properly and retrograde flow of blood occurs.

There are two chronic venous diseases in which incompetence of venous valves is thought to be an important factor in the pathophysiology. These are varicose veins and chronic deep venous insufficiency.

The varicose vein condition consists of dilatation and tortuously of the superficial veins of the lower limb and resulting cosmetic impairment, pain and ulceration. Primary varicose veins are the result of primary incompetence of the venous valves separating the superficial venous system from the deep venous system. Secondary varicose veins occur as the result of deep venous hypertension which has damaged the valves of the perforating veins.

Chronic deep venous insufficiency consists of deep hypertension of the lower limb with associated pigmentation, pain, swelling, ulceration and varicose veins.

For the sake of convenience, the invention will be described in relation to the correction of incompetent valves in the venous system of the lower limb in man, but, it is to be understood that the invention is not limited thereto.

The venous system of the lower limb consists essentially of the superficial venous system and the deep venous system. The superficial system includes the great saphenous vein and the small saphenous vein. The deep venous system includes the anterior and posterior tibial veins which unite to form the popliteal vein which in turn becomes the femoral vein when joined by the small saphenous vein.

The initial defect in primary varicose veins often involves localized incompetence of a venous valve thus allowing reflux of blood from the deep venous system to the superficial venous system. This incompetence is traditionally thought to arise at the saphenofemoral junction but may also start at the perforators. Thus, gross saphenofemoral valvular dysfunction may be present in even mild varicose veins with competent distal veins. Even in the presence of incompetent perforators, occlusion of the saphenofemoral junction usually normalizes venous pressure.

The initial defect in secondary varicose veins is often incompetence of a venous valve secondary to hypertension in the deep venous system. Since this increased pressure is manifested at many points, correction of one site of incompetence could clearly be insufficient as other sites of incompetence will be prone to develop. Apart from the initial defect, the pathophysiology is similar to that of varicose veins.

Once the initial incompetence occurs, incompetence in other valves in the system will tend to occur secondary to the venous hypertension.

Dilatation of the vein wall, whether idiopathic (primary varicose veins) leads to valvular incompetence. This dilatation may eventually lead to stretching and sclerosis of the valve. Other valves in the system will tend to become incompetent as the reflux of blood causes dilatation of the vein wall. As part of the present invention, it was found that it is possible to reverse or prevent the destructive process by overcoming this dilatation. Even if the vein wall weakness is generalized, as appears to be the case with primary varicose veins, correction of the initial defect will delay or prevent stress being placed no that wall and thus hinder progression of the disease.

Some approaches to restoring competency of incompetent valves have involved venous reconstruction surgery of three basic kinds: venous valve transplants, venous transposition and venous valvuloplasty.

As the term implies, the venous valve transplant approach involves the replacement of the segment of the vein having the incompetent valve with a segment of another vein having a competent valve. The venous transposition approach involves the redirection of the venous system so as to bypass an incompetent valve and venous valvuloplasty involves venous valve reconstructive surgery in which the free length of the valve cusps is reduced by plicating sutures.

These approaches to the prior art are well documented in *A Rational Approach to Surgery of the Chronic Venous Stasis Syndrome* by Harry Schanzer and E Converse Peirce Annuals of Surgery 1982, 195: 25-29 as well as in *Valvuloplasty and Valve Transfer* by Seshadri Raju Inter. Angio. 4 1985 419-424.

A single example on one patient of an experimental technique for treating an incompetent venous valve not involving the above types of venous surgery is described in an article by Dag Hallberg in ACTA CHIR SCAND 138: 143-145, 1972. Hallberg placed a band two or three millimeters larger than the diameter of the view around the vein. The band was made of DACRON™ polyester and polyester and was applied when the patient was in the horizontal position. The band was retained loosely in position by several sutures in the venous adventitia.

Hallberg's method could not restore competence to the majority of the incompetent venous valves. In patients with venous disease, incompetent valves will usually be incompetent in the horizontal as well as the vertical positions. See, for example, *Femoral Vein Reconstruction in the Management of Chronic Venous Insufficiency* by Ferias Ebb. and Chastener R., ARCHIVES OF SURGERY, 1982, 117:1571-1579.

Ferias and Chastener operated no 53 femoral veins in which the valves had been demonstrated pre-operatively to be incompetent. In only one case was the valve noted to be competent when the patient was horizontal at the time of operation. Chastener's approach was to suture the vein to prevent post-operative dilatation.

It is well known that by itself DACRON™ polyester material causes marked fibrosis as well as foreign body reaction. Therefore, DACRON™ polyester cannot alone be considered biocompatible. In fact, DACRON™ polyester has been employed to stimulate fibrotic reactions which incorporate the synthetic fabric into tissue (see: S. Raju, ANN. SURG. (1983) 197, 688-697).

The article *Revasculation of Severely Ischemic Extremities with an Arteriovenous Fistula* by F. W. Blaisdell et al. in AMERICAN JOURNAL OF SURGERY, Volume 112, pages 166-173 discloses problems associated with the use of DACRON™ polyester as an implantable material. In a number of cases, gradual narrowing of arteriovenous fistulas under a woven DACRON™ polyester sleeve was demonstrated.

In physical terms, the Hallberg approach was a static one. Once the cuff was sutured into position, no attempt was made to reduce the diameter of the vein at the valve site to restore competency of the valve. Indeed, Hallberg's single patient experiment was concerned with further dilatation of the vein at the valve site rather than reduction in the diameter of the dilated valve to restore competency.

Reference is also made to published PCT application entitled "Correction of Incompetent Venous Valves" (International Application No. PCT/AU87/0021, International Publication No. WO 88/00454), which is incorporated herein by reference.

BRIEF DESCRIPTION OF THE DRAWING

The present invention will be described in greater detail in the following detailed description, with reference to the accompanying drawings, wherein:

FIG. 1(a) illustrates a top plan view of a right sapheno-femoral design;

FIG. 1(b) illustrates a top plan view of an unnotched design for deep valve repair or valves along the length of the long saphenous system;

FIG. 1(c) illustrates a top plan view of a design for the left sapheno-femoral junction;

FIG. 1(d) illustrates the device of FIG. 1(c) in side view;

FIG. 1(e) illustrates the device of FIG. 1(d) in end view;

SUMMARY OF THE INVENTION

It is therefore the object of the present invention to provide a venous valve cuff for restoring competence to an incompetent venous valve comprising an elongated strap and a buckle integrally formed as a part of the elongated strap. The elongated strap is provided with a tapered end. The buckle is opposite to the tapered end of the cuff and is provided with an opening through which the tapered end can pass. The buckle is provided with sides slightly longer than the width of the strap so that the cuff may have a conical shape. The buckle and cuff are formed from the same composite material.

The elongated strap comprises one or more centrally located holes that aid in calibrating variable diameters of the cuff. The centrally located holes may have three different cuff diameters.

The cuff is provided with a notch positioned near the buckle. The notch has sides that are curved, forming an arc of approximately 15°.

DETAILED DESCRIPTION OF THE INVENTION

The present invention describes a cuff 1 for restoring competence to an incompetent venous valve comprising a textile or woven textile and polymer composite such as an inelastic DACRON™ and silicone external stent that has very little elasticity. The DACRON™ and silicone composite has some shape memory that is useful in resisting the compressive forces exerted by the skin near the cuff 1 that tend to collapse the valve after wound closure. The stent is applied to the circumference of the venous valve to change the internal diameter of the venous valve ring and prevent the upward and lateral motion of the venous valve sinus.

Figure 2:
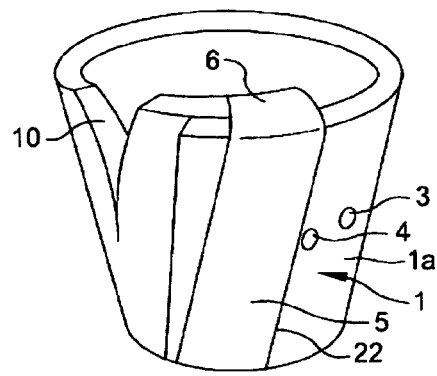
FIG. 2 illustrates in isometric perspective, a valve cuff assembled so that the cranial diameter is greater than the caudal diameter.
Figure 4:
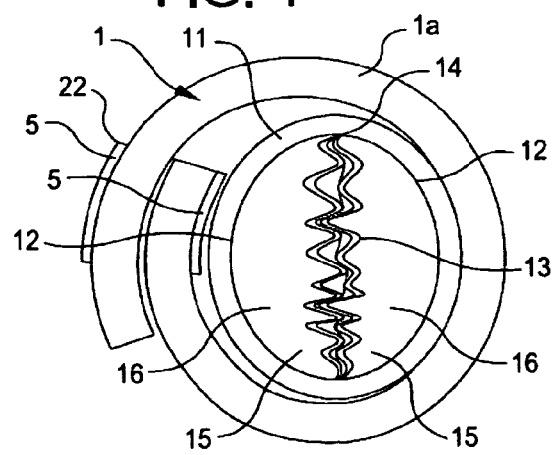
FIG. 4 is a cross section through a cuff and valve.

The diameter of the cuff must be variable and the superficial venous system in a human can vary from 3 mm to 8 mm. The change in diameter of the device must be continuously variable so that it can be changed as the valve is tested. In order to continuously vary the cuff's diameter, the cuff is initially provided as an elongated strap or body 1a which terminates in a buckle 5. Both the strap 1a and the buckle 5 are fabricated from a woven DACRON™ fabric which is coated with a silicon rubber compound. As shown in FIG. 1(e) the buckle 5 surrounds the strap 1 and is bonded or affixed to the strap so that there remains a buckle opening 20 through which the tapered tip 21 of the strap can pass. In practice and as shown in FIGS. 2 and 4, the incompetent valve is buckled into the cuff, whereupon the diameter is fixed via stapling or, suturing to the vein wall.

Often during dissection, the smooth muscle in the venous wall will create a spasm which decreases the amount of incompetence. This tends to cause the operator to leave the cuff diameter too large and when the spasm ceases, incompetence in the long term persists despite the valve being competent at first.

For repairing of the sapheno-femoral junction, data has now been accumulated to indicate that the diameter for the smaller female is approximately 5.5 mm which equates to an internal diameter of 4.5 mm allowing for the thickness of the vein wall at the sapheno-femoral junction itself. There are three centrally located holes 2, 3 and 4 in the body of the cuff 1. These represent calibrations to internal diameters of 4.5 mm, 5.5 mm and 6.5 mm when the leading edge of the buckle 22 is brought into registry with that part of a particular hole which is closest to the tip 21. These three holes equate with internal diameters for a small female at 4.5 mm, an average female at 5.5 mm and a male at 6.5 mm.

There are three principal embodiments. FIG. 1(a) shows the design 7 for the right sapheno-femoral junction or similar tributaries entering the deep systems. In this design, the notch 10 is located near the buckle 5 and along the left edge of the strap 1 in top plan view. FIG. 1(b) shows the unnotched cuff 8 for deep valve repair or valves along the length of the long saphenous system. FIG. 1(c) shows the design 9 for the left sapheno-femoral junction.

Figure 3A:
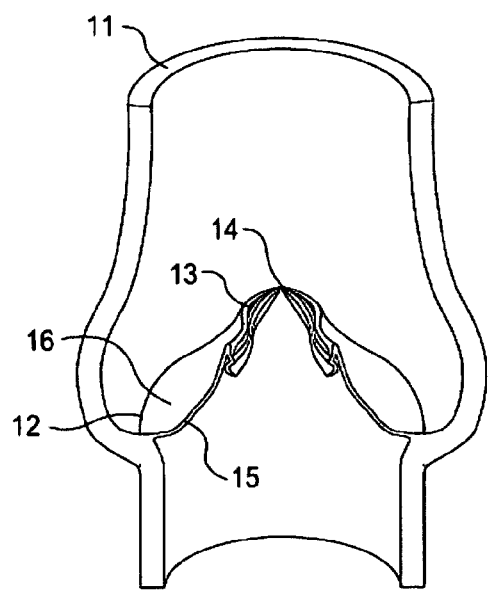
FIG. 3(a) is a cross section perspective view of an incompetent venous valve.
Figure 3B:
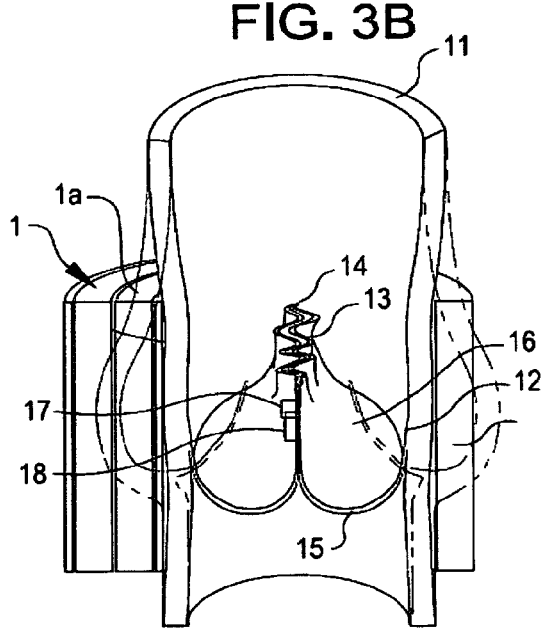
FIG. 3(b) is a perspective view, of a partially cross sectioned of a venous valve after cuff application.

The longitudinal shape of the cuff may be conical if necessary, i.e. the cranial diameter needs to be greater than the caudal diameter, as shown in FIG. 2. The rationale for this design modification derives from a better understanding of venous valve closure. Essentially these facts have been derived through the use of Venoscope. The descending mass of blood creates a downward force on the venous cusps which rotate laterally and upwards compelling the cusps to slam together creating competence. In venous disease the free edges of the valve cusps become floppy and stretch and the valve ring dilates. By allowing the cuff to become conical (larger end up), the tendency for the upward outward motion of the cusps is minimized therefore minimizing the tendency to prolapse as seen in FIG. 3. This improvement in function is made possible by lengthening the buckle 5. Thus, the buckle's sides 6 are slightly longer than would be required if the belt were always at a right angle to the strap 1a. This looseness in the buckle 5 allows the strap 1a to be misaligned slightly so as to allow the cuff 1 to form a cone.

This improvement also allows the reverse to occur i.e. the cuff can be made to be pyramidal (larger end down) in shape. As a result the cuff can be used in some congenital abnormalities of determination of the long saphenous vein. When a double long saphenous system terminates, the join is immediately before the terminal valve at the sapheno-femoral junction. The only way to make the valve competent is to make the caudal diameter less than the cranial diameter. The cuff becomes pyramidal by lengthening the attachments 6 of the buckle 5 to the body of the cuff 1 The cuff can then be sutured in place.

At the sapheno-femoral junction, the venous valves are disposed longitudinally to the skin. Competence is shown to be better achieved if the external valve rings are elliptical in the cross-sectional axis. This is achieved by widening the buckle 5 so that the top of the superficial aspect is flattened. Posterior flattening is achieved by the cuff coming into contact with the common femoral vein or its surrounding adventitia. The reverse is true for the deep venous valve cusps. For repair in the popliteal and tibial systems they are disposed 90° to the skin and therefore the buckle 5 has to be disposed directly on the side wall of the deep vein. The buckle 5 has therefore been increased to accommodate these elliptical changes at smaller diameters (FIG. 4).

Another feature that creates and improves competence at the sapheno-femoral junction is that notch 10 at the superior portion of the cuff 1 has been modified, as shown in FIGS. 1(*a*) and 1(*c*). The modification allows high riding valve cusps to be encircled and therefore decreasing the cuff's diameter In FIG.1(*c*), the notch 10 has a depth d which is half the width of the strap 1*a*. The sides of the notch 10 are curved to define the arc of a circle. The notch angle is set at an arc of approximately 15°. This allows for better fixation of the cuff to the common femoral vein and therefore avoids bulging of the sapheno-femoral junction above the device.

I claim:

1. A venous valve cuff for restoring competence to an incompetent venous valve, comprising:
   (a) an elongated strap;
   (b) a buckle integrally formed as part of said elongated strap,
wherein said strap has a first end portion, a second end portion having a tapered end, and a central portion positioned between said first end portion and second end portion, wherein said buckle is provided with an opening through which said second end portion may pass, and wherein said strap comprises at least one hole located in said central portion, said at least one hole aiding in the calibration of variable diameters of said cuff, wherein said hole designate a cuff diameter selected from a group consisting of 4.5 mm, 5.5 mm, and 6.5 mm.

2. The venous valve cuff according to claim 1 wherein said strap and said buckle are made of a textile and polymer composite.

3. The venous valve cuff according to claim 1 wherein said strap comprises three centrally located holes.

4. The venous valve cuff according to claim 1 wherein said buckle further comprises sides slightly longer than the width of the strap so that said cuff may assume a conical shape during use.

5. The venous valve cuff according to claim 1 wherein said buckle and said cuff are made of the same composite material.

6. The venous valve cuff according to claim 5 wherein said composite material is a DACRON™ and silicone composite.

7. The venous valve cuff according to claim 1 wherein said incompetent venous valve has a superficial aspect, wherein said superficial aspect has a top, and wherein said buckle has a width that allows flattening of the top of said superficial aspect.

8. The venous valve cuff according to claim 1 wherein said cuff further comprises a notch located near said buckle.

9. The venous valve cuff according to claim 8 wherein said notch has sides that are curved.

10. The venous valve cuff according to claim 9 wherein said sides form an arc approximately 15°.

11. A venous valve cuff for restoring competence to an incompetent venous valve, comprising:
    (a) an elongated strap;
    (b) a buckle integrally formed as part of said elongated strap,
wherein said strap has a tapered end and said buckle is provided with an opening through which said tapered end may pass, wherein said strap comprises at least one centrally located hole, said hole aiding in the calibration of variable diameters of said cuff, wherein said hole designate a cuff diameter selected from a group consisting of 4.5 mm, 5.5 mm, and 6.5 mm.

12. The venous valve cuff according to claim 11 wherein said strap and said buckle are made of a textile and polymer composite.

13. The venous valve cuff according to claim 11 wherein said strap comprises three centrally located holes.

14. The venous valve cuff according to claim 11 wherein said buckle further comprises sides slightly longer than the width of the strap so that said cuff may assume a conical shape during use.

15. The venous valve cuff according to claim 11 wherein said buckle and said cuff are made of the same composite material.

16. The venous valve cuff according to claim 15 wherein said composite material is a DACRON™ and silicone composite.

17. The venous valve cuff according to claim 11 wherein said incompetent venous valve has a superficial aspect, wherein said superficial aspect has a top, and wherein said buckle has a width that allows flattening of the top of said superficial aspect.

18. The venous valve cuff according to claim 11 wherein said cuff further comprises a notch located near said buckle.

19. The venous valve cuff according to claim 18 wherein said notch has sides that are curved.

20. The venous valve cuff according to claim 19 wherein said sides form an arc approximately 15°.

* * * * *